United States Patent [19]

Taninaka et al.

[11] 4,080,466
[45] Mar. 21, 1978

[54] PHARMACEUTICAL COMPOSITIONS CONTAINING 4-HYDROXYL-1,3-DITHIOLAN-2-YLIDENE MALONATES

[75] Inventors: Kuniaki Taninaka, Ibaragi; Hitoshi Kurono, Amagasaki; Tsutomu Kasai, Sakai, all of Japan

[73] Assignee: Nihon Nohyaku Co., Ltd., Tokyo, Japan

[21] Appl. No.: 759,358

[22] Filed: Jan. 14, 1977

Related U.S. Application Data

[63] Continuation-in-part of Ser. No. 584,409, Jun. 6, 1975, abandoned.

[30] Foreign Application Priority Data

May 28, 1976 Japan .................................. 51-61910

[51] Int. Cl.² ............................................ A61K 37/00
[52] U.S. Cl. .................................................... 424/277
[58] Field of Search ........................................ 424/277

[56] References Cited

U.S. PATENT DOCUMENTS 3,761,596  9/1973  Taninaka et al. .................... 424/277

*Primary Examiner*—Frederick E. Waddell
*Attorney, Agent, or Firm*—Karl W. Flocks

[57] ABSTRACT

A 1,3-dithiolan-2-ylidene malonate derivative having the formula,

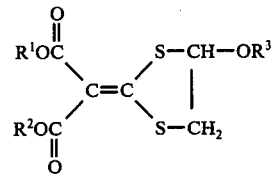

wherein $R^1$ and $R^2$, which may be the same or different, represent individually a $C_1$–$C_4$ alkyl group; and $R^3$ represents a hydrogen atom, an acetyl group or a propionyl group, has effects of stimulating, improving and recovering the functions of livers, and can prevent, alleviate and cure various liver damages of humans and animals when administered thereto either orally or parenterally.

34 Claims, No Drawings

PHARMACEUTICAL COMPOSITIONS CONTAINING 4-HYDROXYL-1,3-DITHIOLAN-2-YLIDENE MALONATES

The present application is a continuation-in-part of my copending application No. 584409 filed June 6, 1975, now abandoned.

This invention relates to a process for controlling the liver damages of humans and animals, and to a pharmaceutical composition for use in said process.

More particularly, the invention is concerned with a pharmaceutical composition containing an effective amount of a compound represented by the general formula (I),

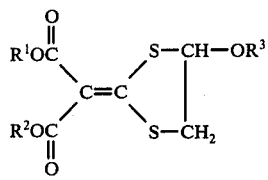

wherein $R^1$ and $R^2$, which may be the same or different, represent individually a $C_1$-$C_4$ alkyl group; and $R^3$ represents a hydrogen atom, an acetyl group or a propionyl group.

The invention further relates to a pharmaceutical composition in the form of administration unit which contains a compound of the above-mentioned general formula (I) as active ingredient, either alone or in admixture with a pharmaceutically acceptable diluent.

The invention further pertains to a process for controlling the liver damages of humans and animals which comprises administering to the humans or animals a pharmaceutical composition in the form of administration unit which contains a compound of the above-mentioned general formula (I) as active ingredient, either alone or in admixture with a pharmaceutically acceptable diluent.

The term "controlling the liver damages" or the like, referred to in the body and the claims, means to prevent, alleviate or cure the liver damages.

In view of its various functions, the liver is frequently called a delicate chemical factory. Thus, in the liver, various chemical reactions are being biochemically effected, such as detoxication, sugar metabolism, protein metabolism, lipid metabolism, formation and secretion of bile, control of hormones, formation of blood coagulant prothrombin, regeneration of liver cells, and storage of various living body-constituting elements (fats, glycogens, proteins and vitamins).

However, even such delicate and well-balanced functions of the liver sometimes undergo damages, either acutely or chronically, due to various factors such as alcohols, insufficient nutrition, viruses, chemicals, toxicants, etc. to cause such diseases as, for example, hepatitis, liver necrosis, fatty liver and cholestasis.

As the result of extensive studies, the present inventors have found that the compounds represented by the aforesaid general formula (I) have actions to activate liver cells and to activate various metabolic functions of the liver, such as sugar metabolism, detoxication, formation and excretion of bile flow and biliary salts (choleretic action), and hence can improve the damaged liver functions to provide such pharmacological effects as to alleviate or cure the damages and to protect the liver functions from certain damages.

An object of the present invention is to provide a novel pharmaceutical composition usable for controlling the liver damages of human and animals.

Another object of the invention is to provide a process for controlling the liver damges of humans and animals.

Other objects and advantages of the invention will become apparent from the following description.

The compounds represented by the aforesaid general formula (I) partly include known compounds. Dialkyl 4-acetoxy-1,3-dithiolan-2-ylidene malonates, which are the compounds of the general formula (I) when $R^3$ is an acetyl group, for example can be synthesized by reacting a dialkali 2,2-bis(alkoxycarbonyl)-1,1-ethylene dithiolate with a 1-acetoxy-1,2-dihalogenoethane in the presence of a suitable base. This reaction may be represented by the following reaction scheme:

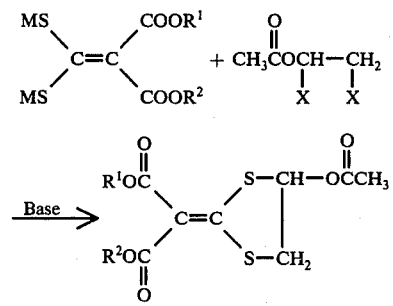

wherein $R^1$ and $R^2$ are as defined previously; M represents an alkali metal atom; and X represents a halogen atom. Examples of the suitable base usable in the above reaction include sodium hydroxide, potassium hydroxide, sodium hydride, metallic sodium and t-amyl alcoholate, and examples of suitable solvent include water, alcohols, acetone, benzene, tetrahydrofuran, ether, dioxane, acetonitrile, dimethyl formamide and dimethyl sulfoxide. Ordinarily, the reaction proceeds at a temperature in the range from about 5° to 70° C. After completion of the reaction, the resulting end compound is recovered according to an ordinary procedure. This compound may be prepared by acylating a dialkyl 4-hydroxy-1,3-dithiolan-2-ylidene malonate with desired acylating agent such as acetic or propionic acid anhydride or chloride. Further, dialkyl 4-hydroxy-1,3-dithiolan-2-ylidene malonates, which are the compounds of the general formula (I) when $R^3$ is a hydrogen atom, can be synthesized by hydrolyzing a corresponding 4-acyloxy compound. When a 4-acetoxy compound, for example, is used as starting material, the above reaction may be represented by the following reaction scheme:

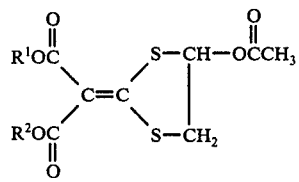

-continued

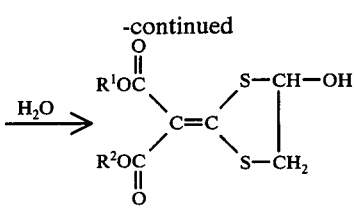

wherein $R^1$ and $R^2$ are as defined previously. The hydrolysis reaction can effectively be promoted in the presence of an acid. Examples of the acid include inorganic acids such as sulfuric, hydrochloric and phosphoric acids, and organic acids such as p-toluenesulfonic, benzenesulfonic and oxalic acids. As the solvent, water may be used. Generally, however, the use of water in combination with an inert organic solvent is effective, and there is used such water-miscible solvent as dioxane, acetone, dimethyl formamide, dimethyl sulfoxide or tetrahydrofuran. The reaction temperature may be properly decided within the range from about room temperature to 100° C, though this is not limitative. After completion of the reaction, the reaction product is recovered according to an ordinary procedure.

In the same manner as above, it is possible to prepare all the compounds represented by the general formula (I) which are used in the present invention.

Typical examples of the compounds represented by the general formula (I) are as shown in Table 1.

Table 1

| No. | Compound | |
|---|---|---|
| (1) | Diethyl 4-hydroxy-1,3-dithiolan-2-ylidene malonate | m.p. 62 – 63° C |
| (2) | Diisopropyl 4-hydroxy-1,3-dithiolan-2-ylidene malonate | m.p. 73 – 74° C |
| (3) | Diisobutyl 4-hydroxy-1,3-dithiolan-2-ylidene malonate | $n_D^{20}$ 1.5493 |
| (4) | Ethyl isopropyl 4-hydroxy-1,3-dithiolan-2-ylidene malonate | $n_D^{25}$ 1.5646 |
| (5) | Diethyl 4-acetoxy-1,3-dithiolan-2-ylidene malonate | $n_D^{20}$ 1.5596 |
| (6) | Diethyl 4-propionyloxy-1,3-dithiolan-2-ylidene malonate | $n_D^{20}$ 1.5505 |
| (7) | Diisopropyl 4-acetoxy-1,3-dithiolan-2-ylidene malonate | m.p. 81 – 82° C |
| (8) | Diisopropyl 4-propionyloxy-1,3-dithiolan-2-ylidene malonate | $n_D^{20}$ 1.5344 |
| (9) | Di-n-propyl-4-acetoxy-1,3-dithiolan-2-ylidene malonate | $n_D^{20}$ 1.5455 |

The compounds represented by the general formula (I) are extremely low in toxicity to mammals, and their acute oral toxicity to male mice expressed as $LD_{50}$ values are at such a low toxicity level as in the range from 1,000 to 6,000 mg/kg or more, in general. For example, the $LD_{50}$ value of the compound 2 in Table 1 is more than 6,590 mg/kg. Further, these compounds have no detrimental effects on test animals administered therewith, so far as the doses thereof are within an ordinary administration range.

The compounds of the general formula (I) are usable as pharmaceuticals for humans and animals. They have broad and various pharmaceutical spectra. The compound of the formula (I) has effects of stimulating, improving and recovering the functions of livers, and can prevent, alleviate or cure various liver damages of humans and animals when administered thereto either orally or parenterally.

Experimental liver damages such as liver necrosis, hepatitis and fatty liver induced by administering chemicals such as carbon tetrachloride, chloroform, bromobenzene, dimethyl-nitrosoamine, thioacetamide, allyl alcohol, D-galactosamine or ethionine to animals, have been acknowledged as the models of human liver damages against which parmaceuticals are sought.

Further, liver damages caused by toxic inorganic salts such as cadmium and selenium salts can be alleviated when they are administered.

They can show in animal tests such main effects as described below.

(1) The compounds of the present invention have effects of not only preventing all of the above experimental damages but also alleviating or curing the experimental hepatitis and fatty liver. Thus, they will be appreciated as pharmaceuticals usable for those purposes.

(2) They have actions to stimulate the alcohol metabolism function of the liver to lower the concentration of alcohol in the blood, and hence are effective for promotion of recovery from alcoholic intoxication and for prevention, alleviation and therapy of crapulence.

(3) They have actions to stimulate the sugar metabolic function of the liver to lower the abnormally elevated concentration of sugar in the blood, and hence are effective as blood sugar depressants and curatives for diabetes.

(4) They have action to stimulate the formation and the excretion of bile flow or biliary salts.

(5) When cadmium or selenium salts are administered to animals, which have previously been administered with the said compounds, the toxic symptoms caused by said salts are far more alleviated than in the case of blank animals.

Accordingly, the compounds represented by the general formula (I) are effective as preventives, alleviatives and curatives for liver damages, acute hepatitis, chlonic hepatitis, fatty liver diseases and chemical poisoning. Further, the said compounds are effective as depressants of alcohol in the blood, blood sugar depressants, diabetes curatives, cholestasis including the formation and the excretion of bile flow or biliary salts, and drugs for stimulating, promoting, improving and recovering metabolic functions of the livers.

In using the said compounds as the above-mentioned drugs, they may be formulated, according to usual procedures and means adopted in this field, into pharmaceutical compositions in the form of administration units convenient for their individual application purposes. That is, the said compounds are formulated into pharmaceutical compositions, either alone or in admixture with a pharmaceutically acceptable diluent, which may be any one of solids, semi-solids, liquids and intakable capsules, and are administered to humans or animals, either orally or parenterally.

Thus, the present invention provides a pharmaceutical composition which comprises the above-mentioned compound as active ingredient and, in admixture therewith, a pharmaceutically acceptable solid, semi-solid or liquid diluent.

The present invention further provides a pharmaceutical composition containing as active ingredient the above-mentioned compound in the form of a sterile and/or isotonic aqueous solution.

The present invention still further provides a pharmaceutical composition in the form of administration unit which contains the above-mentioned compound either alone or in admixture with a pharmaceutically acceptable diluent.

The pharmaceutical compositions of the present invention can be provided in such various administration unit forms as powders, granules, tablets, sugar-coated tablets, pills, capsules, suppositories, suspensions, liquids, emulsions, ampoules and injections.

The present invention includes such mode that the above-mentioned compound as active ingredient is administered singly. The present invention further includes such mode that the above-mentioned compound is administered in the form of a mixture with a pharmaceutically acceptable diluent. The diluent referred to herein means not only a mere diluent but also a pharmaceutically acceptable usual adjuvant. Examples of the mere diluent are those which are ordinarily used in the pharmaceutical field, and include such solid diluents as starch, lactose, calcium hydrogen phosphate, heavy magnesium oxide and the like, and such liquid diluents as water, isotonic solution, glucose solution and the like. Examples of the adjuvant include vehicles, extenders, binders, wetting agents, disintegrators, surfactants, lubricants, dispersants, buffer agents, seasonings, deodorants, dyes, flavors, preservatives and dissolution aids, though these are not limitative. These adjuvants may be used either singly or in the form of a mixture of two or more members.

The pharmaceutical composition of the present invention may be prepared according to any known method. For example, a mixture of the active ingredient and a diluent is formed, for example, into granules, and the thus formed granular composition is molded, for example, into tablets. In case the pharmaceutical composition is for parenteral administration, it is preferable to be made aseptic and, if necessary, be made isotonic to the blood.

Generally, the pharmaceutical composition of the present invention contains about 0.01 to 100% by weight, based on the weight of the composition, of the active compound. Thus, the present invention includes such mode that the said compound is used independently.

The pharmaceutical composition of the present invention may be incorporated with other pharmaceutically active compound. In some cases, the composition may be incorporated with a plurality of the present compounds.

For the control of various liver damages and various diseases derived therefrom, the pharmaceutical composition of the present invention may be applied to humans and animals according to an ordinary procedure adopted in this field, in order to attain such effects as shown in the aforesaid animal tests. Thus, the composition of the present invention is administered orally or parenterally. The oral administration includes sublingual administration, and the parenteral administration includes administration by way of injection including, for example, subcutaneous, intramuscular and intravenous injections and instillation.

The dose of the pharmaceutical of this invention varies depending on many factors, including the kind of subject (whether the pharmaceutical is administered to humans or to animals), the difference in susceptibility, age, sex, body weight, the clinical picture, the physical conditions of patients, the means of administration, the time and interval of administration, the kind and properties of pharmaceutical composition, the kind of active ingredient, etc. In some cases, accordingly, the dose of the pharmaceutical may be made smaller than the minimum dose mentioned below, while in other cases the dose would be in excess of the maximum dose mentioned below. In case the pharmaceutical is to be administered in a large dose, it is preferable that the pharmaceutical is divisionally administered several times a day.

In the case of oral administration, effective dose for animals is in the range from 0.1 to 500 mg, preferably from 1 to 100 mg, of active ingredient per one kilogramme body weight per day. In the case of parenteral administration, effective dose for animals is in the range from 0.01 to 250 mg, preferably from 0.1 to 25 mg, of active ingredient per one kilogramme body weight per day.

In the case of oral administration, effective dose for humans, deduced from the above-mentioned effective dose for animals with consideration for susceptibility difference and security, is advantageously in the range from 0.1 to 250 mg, preferably from 0.5 to 50 mg, per one kilogramme body weight per day. In the case of parenteral administration, effective dose for humans is in the range from 0.01 to 100 mg, preferably from 0.1 to 25 mg, per one kilogramme body weight per day.

The present invention is illustrated in more detail below with reference to examples including synthesis examples, but the invention is not limited to the examples. In Examples 1 to 8, all parts are by weight.

SYNTHESIS EXAMPLE 1

Synthesis of diisopropyl 4-hydroxy-1,3-dithiolan-2ylidene malonate:

10.5 Grams of diisopropyl 4-acetoxy-1,3-dithiolan-2-ylidene malonate was dissolved in a mixed solvent comprising 50 ml of dioxane and 10 ml of water. To the resulting solution was added with stirring 3.4 g of 35% hydrochloric acid, and the resulting mixture was heated in a hot water bath at 80° C for 2 hours. Thereafter, the reaction liquid was cooled to room temperature, and then extracted with 100 ml of benzene. The benzene layer was sufficiently washed with water, dried with anhydrous sodium sulfate and then subjected to filtration. Subsequently, the sodium sulfate was removed, and a major portion of the benzene was removed by distillation under reduced pressure. To the residue, n-hexane was added to deposit white crystals, which were then recovered by filtration to obtain the above-mentioned compound in the form of white crystals, m.p. 73° – 74° C, yield 87%.

SYNTHESIS EXAMPLE 2

Synthesis of diethyl 4-hydroxy-1,3-dithiolan-2-ylidene malonate:

To a solution of 29 g of diethyl 4-acetoxy-1,3-dithiolan-2-ylidene malonate in 120 ml of acetone was added with stirring 50 ml of 50% sulfuric acid. The resulting mixture was heated in a hot water bath at 70° C for 1 hour. Therfater, the reaction liquid was cooled to room temperature, and then extracted with 200 ml of benzene. Subsequently, the benzene layer was treated in the same manner as in Synthesis Example 1 to obtain the above-mentioned compound in the form of white crystals, m.p. 62° – 63° C, yield 70%.

SYNTHESIS EXAMPLE 3

Synthesis of diisopropyl 4-acetoxy-1,3-dithiolan-2-ylidene malonate:

To a mixture comprising 18.8 g of diisopropyl malonate and 7.6 g of carbon disulfide was gradually added with stirring at 10° to 15° C, 20 ml of water containing 8 g of sodium hydroxide. The resulting mixture was reacted at said temperature for 1 hour, and then charged with 100 ml of acetone. Into this mixture was gradually dropped 15.7 g (0.1 mole) of 1,2-dichloroethyl acetate, and the mixture was heated with stirring at 60° to 70° C for 2 hours. After completion of the reaction, excess acetone was removed by distillation, whereby white solids deposited. Subsequently, the deposited solids were recrystallized from n-hexane to obtain 24.3 g of the above-mentioned compound in the form of white solids, m.p. 81° – 82° C, yield 72.5%.

SYNTHESIS EXAMPLE 4

Synthesis of diethyl 4-propionyloxy-1,3-dithiolan-2-ylidene malonate:

27.5 Grams (0.1 mole) of a diethyl ester of 4-hydroxy-1,3-dithiolan-2-ylidene malonic acid and 7.9 g (0.1 mole) of pyridine were dissolved in 200 ml of ether. Into the resulting solution, 13 g (0.1 mole) of a propionic anhydride was gradually dropped. After completion of the dropping, the resulting mixture was stirred at said temperature for 1 hour, and then poured into water to form an ether layer containing a yellow oily substance. The ether layer was washed with water, dried and then subjected to distillation to obtain 28.6 g of the above-mentioned compound in the form of an oily substance, $n_D^{20} = 1.5505$, yield 86.5%.

SYNTHESIS EXAMPLE 5

Synthesis of diethyl 4-hydroxy-1,3-dithiolan2-ylidene malonate:

9.5 Grams (0.03 mole) of diethyl 4-acetoxy1,3-dithiolan-2-ylidene malonate were dissolved in 50 ml of dioxane. To the solution was added 60 ml of 30% (by weight) sulfuric acid solution (0.18 mole). The resulting mixture was heated with stirring at 60° to 80° C under reflux. After completion of the reactions, the mixture was cooled, and the product was extracted with 200 ml of benzene, washed with an aqueous solution of sodium hydrogencarbonate and then with water, and dried. After distillation of benzene, 2.5 g of the above-mentioned compound was obtained in the form of white crystals, m.p. 62° –°63° C, yield 90%.

EXAMPLE 1

| Compound 1 | 10 parts |
|---|---|
| Heavy magnesium oxide | 10 parts |
| Lactose | 80 parts |

The above-mentioned components were homogeneously mixed and pulverized to obtain a powder.

EXAMPLE 2

| Compound 2 | 10 parts |
|---|---|
| Synthetic aluminum silicate | 10 parts |
| Calcium hydrogenphosphate | 5 parts |
| Lactose | 75 parts |

The above-mentioned components were treated in the same manner as in Example 1 to obtain a powder.

EXAMPLE 3

| Compound 2 | 50 parts |
|---|---|
| Starch | 10 parts |
| Lactose | 15 parts |
| Crystalline cellulose | 20 parts |
| Polyvinyl alcohol | 5 parts |
| Water | 30 parts |

The above-mentioned components were homogeneously kneaded, granulated, dried and sieved to obtain a granule.

EXAMPLE 4

99 Parts of the granule obtained in Example 3 was incorporated with 1 part of calcium stearate, and then subjected to compression molding to obtain a tablet of 10 mm in diameter.

EXAMPLE 5

| Compound 4 | 95 parts |
|---|---|
| Polyvinyl alcohol | 5 parts |
| Water | 30 parts |

The above-mentioned components were treated in the same manner as in Example 3 to obtain a granule. 90 Parts of the thus obtained granule was incorporated with 10 parts of crystalline cellulose, and then subjected to compression molding to obtain a tablet of 8 mm in diameter. Further, this tablet was formed into a sugar-coated tablet by use of proper amounts of a suspension comprising ethanolic shellac, syrup gelatin and precipitated calcium carbonate, and a dye.

EXAMPLE 6

| Compound 4 | 4 parts |
|---|---|
| Nonionic surfactant | 10 parts |
| Isotonic sodium chloride solution | 86 parts |

The above-mentioned components were mixed together with heating to form a solution, which was then cooled to obtain an injection.

EXAMPLE 7

| Compound 2 | 0.5 part |
|---|---|
| Nonionic surfactant | 2.5 parts |
| Distilled water for injection | 97.0 parts |

The above-mentioned components were treated in the same manner as in Example 6 to obtain an injection.

EXAMPLE 8

The powder obtained in Example 1 was filled into commercially available capsules to prepare a capsule.

EXAMPLE 9

Protective Effect on Acute Liver Damage associated with Centrilobular Necrosis (Experimental Model using Carbon Tetrachloride)

Carbon tetrachloride ($CCl_4$) administration induces centrilobular necrosis of the liver associated with loss of diphosphopyridine nucleotide, hepatic glycogen, coenzyme A and increase in neutral fat. Release of several enzymes from the hepatocytes, and increase of enzyme activities in the plasma are recognized as the result of the damage of the liver. A suitable means for evaluating the degree of damage induced by $CCl_4$ or the degree of protection afforded by drugs is to study the plasma glutamic-pyruvic transminase (p-GPT) activity.

Methods: The test compounds were dissolved or suspended in olive oil and administered orally at the dose of 250 mg/kg to the mice (Four-week-old male mice-dd strain). After 6 hours, $CCl_4$ was administered orally (0.05 ml/kg as olive oil solution). Animals were killed 24 hours after CCl₄ administration, and the liver was grossly observed. The plasma was obtained by centrifugation. Activities of p-GPT were determined by the method of Reitman and Frankel and expressed in Karmen units.

Score for liver damage index was as follows:

| Liver damage index | Description |
| --- | --- |
| 0 | Normal |
| 2 | Slightly recognized |
| 4 | Clearly observable damage |
| 6 | Heavy damage |

Each figure indicates average of 5 to 6 mice. Values of p-GPT over 1,000 Karmen unit regarded as 1,000 for calculation of average for convenience.

Table 2

| Compd. No. | Results: Liver damage Index | p-GPT |
| --- | --- | --- |
| 1 | 0.5 | 66 |
| 2 | 0.1 | 20 |
| 3 | 0.3 | 52 |
| 4 | 0.1 | 40 |
| 5 | 1.2 | 106 |
| 6 | 1.4 | 210 |
| 7 | 0.4 | 80 |
| 8 | 0.6 | 62 |
| 9 | 0.8 | 102 |
| Carbon tetrachloride alone | 5.2 | >1,000 |
| Thioctic acid amide | 4.8 | 763 |
| Anethol trithion | 1.6 | 38 |
| Non-treatment | 0.0 | 35 |

Carbon tetrachloride is best suitable for bringing test animals to the state of acute hepatitis. As is clear from the results of tests carried out by use of carbon tetrachloride, all the active ingredients used in the present composition show prominent liver damage-preventing effects, and are comparable in effectiveness to thioctic acid amide and anethol trithion which are commercially available at present as liver drugs.

Accordingly, the compounds of this invention are useful as pharmaceutical for human and animal acute hepatitis.

somewhat chronic liver damages, and then the present compounds were administered thereto to know whether or not the compounds were effective against chronic hepatitis.

The degree of the liver damage and the therapeutic effects of the compounds were evaluated according to BSP test. The BSP test is a method in which BSP (sulfobromophthalein sodium), a dye known to be quickly metabolized in and excreted from the liver, is intravenously injected into animals and, after a definite period of time, the blood is taken out to measure the amount of BSP remaining in the plasma. In case the animals are suffering from the lever damage, the dye will remain, according to the degree of the damage, at the stage where a major portion of BSP metabolized and excreted in the case of normal animals.

Five groups of rats (Spraque Dawley strain) were treated as follows:

Group A: The rats were orally administered with 100 mg/kg of thioacetamide, at 3 days intervals for 36 days (12 times of the administration), then were submitted for 10 days to a normal diet.

Group B: The rats were orally administered with 100 mg/kg of thioacetamide at 3 days intervals for 36 days (12 times of the administration), then were submitted for 10 days to the normal diet + 0.2% of compound 4.

Group C: The rats were orally administered with 100 mg/kg of thioacetamide at 3 days intervals for 36 days (12 times of the administration), then were submitted for 10 days to the normal diet + 0.2% of compound 2.

Group D: The rats were orally administered with 100 mg/kg of thioacetamide at 3 days intervals for 36 days (12 times of the administration), then were submitted for 10 days to the normal diet + 0.2% of anethol trithion.

Group E: The rats were submitted to the normal diet as the control.

Five rats were sacrificed from each group at appropriate intervals for BSP (sulfobromophthalein) test, the results of which were shown as amounts (mg) of BSP remaining in 1 dl of plasma.

Table 3

| Time of sacrifice | Group A | Group B | Group C | Group D | Group E |
| --- | --- | --- | --- | --- | --- |
| 24 hr after 4 times TAA administration | | 18.2±2.6 | | | 0.3±0.1 |
| 24 hr after 8 times TAA administration | | 16.8±5.2 | | | — |
| 24 hr after 12 times TAA administration | | 17.3±4.4 | | | 0.8±0.1 |
| After compounds administration | | | | | |
| 2 Days | 12.7±3.7 | 7.2±1.2 | 7.0±2.8 | 9.7±4.1 | 0.4±0.1 |
| 5 Days | 8.7±1.9 | 3.6±0.5 | 3.1±0.7 | 7.3±3.4 | — |
| 10 Days | 1.4±0.4 | 0.3±0.1 | 0.8±0.2 | 0.9±0.1 | 0.6±0.1 |

EXAMPLE 10

Therapeutic Effect on Chronic Liver Damage (Experimental Model Using Thioacetamide)

Thioacetamide (hereinafter abbreviated to "TAA") also causes liver damages in animals, like carbon tetrachloride, and hence is frequently used as a chemical for bringing about hepatitis and fatty liver diseases. In the tests of this Example, TAA was repeatedly administered to animals to prepare test animals suffering from By the repeated administration of TAA, the concentration of BSP in the blood increased to 16 to 19 mg/dl and the said level lasted, and therefore it is considered that the rats were brought to a state close to chronic hepatitis. After the administration of TAA, the present compound-administered groups (Groups B and C) were quicker in cure of lever damage than the unadministered group (Group A). This indicates that the present compounds are effective against chronic hepatitis as well.

EXAMPLE 11

Protective Effect on Acute Liver Damage associated with Periportal Necrosis (Experimental Model using Allyl Alcohol)

Methods:

The compund of this invention or anethol trithion was orally administered to the male mouse (4 week-old, dd-strain) at the dose of 100 mg/kg. Six hours after it, allyl alcohol was orally administered at the dose of 0.075 mg/kg. Twenty four hours after it, the animals were sacrificed to collect blood samples. BSP test revealed the residual quantity of BSP, from which the protective effect of the compound of this invention was evaluated.

Table 4

Results:
Protective effect on acute hepatitis associated with periportal necrosis

| Hepato-toxin | Index of hepato-toxicity | Control* | Positive** control | Compound** 2 | Anethol** trithion |
|---|---|---|---|---|---|
| Allyl alcohol | BSP | 1.8 ± 0.4 | 28.4 ± 4.8 | 17.1 ± 3.8 | 19.3 ± 4.6 |

*The hepatotoxin alone was administered.
**After a pretreatment with the compound of this invention, the hepatotoxin was given.

Allyl alcohol differs from carbon tetrachloride or bromobenzene, dimethylnitrosamine or chloroform in that it induces liver damage associated with periportal necrosis. As shown in Table 4, the compound of this invention protected the liver damage.

Accordingly, the compound of this invention is useful as a pharmaceutical for human or animal liver disease accompanied with periportal necrosis.

EXAMPLE 12

Protective Effect on Acute Hepatitis associated with Mesenchymal Reaction and Discrete Lobular Necrosis (Experimental Model using D-Galactosamine)

D-Galactosamine is a compound which induces a discrete lobular necrosis associated with mesenchymal reaction similar to the change observed in human viral hepatitis, so that it is frequently used in producing a model for viral hepatitis.

Methods:

The compound of this invention or anethol trithion was administered orally to the male rat (SD strain) at the dose of 100 mg/kg. Six hours after it, D-galactosamine was intraperitoneally administered at the dose of 600 mg/kg. Four hours after it, an additional 300 mg/kg was administered intraperitoneally. Eight hours after it, the animals were sacrificed to collect the blood samples. P-GPT activity and triglyceride in the liver were measured to evaluate the effect of the compound of this invention.

Table 5

Results:
Protective effect on acute liver damage associated with discrete lobular necrosis

| Hepato-toxin | Index of hepatotoxicity | Control | Positive* control | Compound** 2 | Anethol** trithion |
|---|---|---|---|---|---|
| D-Galactos-amine | $p$-GPT (Karmen unit) | 13 ± 0.5 | 92 ± 59 | 73 ± 13 | 106 ± 30 |
| | Triglyceride in liver (mg/g) | 6.5 ± 12 | 8.2 ± 2.2 | 7.0 ± 0.82 | 9.2 ± 1.5 |

*The hepatotoxin alone was administered.
**After a pretreatment with Compound 2 or anethol trithion, the hepatotoxin was given.

As shown in Table 5, the compound of this invention protected the liver damage.

Accordingly, the compound of this invention is useful as a pharmaceutical for use in therapying human or animal hepatitis accompanied with mesenchymal reaction and discrete lobular necrosis.

EXAMPLE 13

Effect on Fatty Liver (Experimental Models using Ethionine)

There are known many factors inducing fatty liver. But, the fatty liver is grouped into a couple of patterns from the mechanism of lipid accumulation or metabolism of lipoprotein in the liver. Ethionine is a typical example which induces first pattern of fatty liver. It inhibits RNA and protein synthesis and destructs polysome of the liver cell. Fatty liver is induced by inhibition of the protein synthesis and disturbance of lipoprotein secretion.

Usually, fatty liver is closely related to the accumulation of triglyceride in the liver. In the present example, the degree of fatty liver and protective or therapeutic effect against the fatty liver was evaluated by measurement of triglyceride content in the liver. Methods:

The compounds of this invention and methionine were independently dissolved or suspended into olive oil and administered orally to 4 week-old male mouse (dd-strain) at the dose of 250 mg/kg. One hour before it, simultaneously to it, or one hour after it, ethionine dissolved in equimolar NaOH solution was administered intraperitoneally at the dose of 200 mg/kg. Twenty four hours after the administration of ethionine, the animals were sacrificed and triglyceride content in the liver was determined by chromotropic acid method.

Table 6

Results: Effect on fatty liver

| Group | | Number of animals | Triglyceride (mg/g-liver) |
|---|---|---|---|
| | Control | 10 | 5.8 ± 0.43 |
| | Ethionine (positive control) | 10 | 15.6 ± 1.34 |
| | Compound 4 → 1 hr → Ethionine | 10 | 12.0 ± 0.77 |
| Compound 4 | Compound 4 → 0 hr → Ethionine | 10 | 6.7 ± 0.43 |
| | Ethionine → 1 hr → Compound 4 | 10 | 12.8 ± 0.92 |
| | Compound 1 → 1 hr → Ethionine | 10 | 12.3 ± 0.82 |
| Compound 1 | Compound 1 → 0 hr → Ethionine | 10 | 7.1 ± 0.24 |
| | Ethionine → 1 hr → Compound 1 | 10 | 11.8 ± 0.72 |
| | Compound 2 → 1 hr → Ethionine | 10 | 10.3 ± 0.96 |
| Compound 2 | Compound 2 → 0 hr → Ethionine | 10 | 6.9 ± 0.38 |
| | Ethionine → 1 hr → Compound 2 | 10 | 11.8 ± 0.39 |
| Methionine + Ethionine | Methionine → 0 hr → Ethionine | 10 | 10.8 ± 0.88 |

As above, the compounds of this invention depressed the abnormal accumulation of triglyceride, induced by ethionine, in the liver to exhibit a protective and therapeutic effect against fatty liver. The compounds of this invention were superior to methionine in the above-mentioned effect. Accordingly, the compounds of this invention are useful as pharmaceutical for use in therapying fatty liver in humans and animals.

EXAMPLE 14

Therapeutic Effect on Fatty Liver (Experimental Model using Carbon Tetrachloride)

Carbon tetrachloride also induces fatty liver, but the picture of disease differs from the case of ethionine-induced fatty liver. Carbon tetrachloride is generally considered to damage microsome and thereby to inhibit protein synthesis and induce fatty liver. Methods:

Carbon tetrachloride was subcutaneously administered to 35 week-old male rats (SD strain) for 4 days at the dose of 1 mg/kg. The treated animals were left for 3 days after the last administration to maximize the manifestation of fatty liver.

Administration of the compounds of this invention was commenced on the fourth day after the administration of carbon tetrachloride was completed. It was orally given everyday for 10 days at the dose of 50 or 250 mg/kg. On the 11th day, the animals were sacrificed. The therapeutic effect was evaluated by determining the content of liquid in the liver (triglyceride and total lipid) and examining the histopathological changes. Triglyceride and total lipid were determined colorimetrically by chromotropic acid method and Bragdon's oxidation method, respectively.

Indices for the histopathological change is as follows:

| Index | Histopathological changes |
|---|---|
| − | Normal |
| ± | Formation of small droplet deposition of lipid but the number of droplet is not so many. |
| + | Formation of small or slightly fused droplet deposition of lipid and increasing the number of droplet |
| ++ | Formation of fused large droplet deposition of lipid |

Table 7

Results: Therapeutic effect on fatty liver

| Group | Triglyceride (mg/g-liver) | Total lipid (mg/g-liver) |
|---|---|---|
| Control | 10.9 ± 2.8 | 59.6 ± 7.6 |
| Positive control | 53.6 ± 9.2 | 178.3 ± 21.5 |

Table 7-continued

Results: Therapeutic effect on fatty liver

| Group | Triglyceride (mg/g-liver) | Total lipid (mg/g-liver) |
|---|---|---|
| Compound 4 (50 mg/kg) | 40.6 ± 8.2 | 87.6 ± 7.2 |
| ibid. (250 mg/kg) | 25.3 ± 4.2 | 70.3 ± 7.7 |
| Compound 1 (50 mg/kg) | 36.2 ± 7.8 | 80.2 ± 9.8 |
| ibid. (250 mg/kg) | 24.9 ± 8.2 | 70.3 ± 10.2 |
| Compound 2 (50 mg/kg) | 38.6 ± 8.5 | 82.3 ± 15.1 |
| ibid. (250 mg/kg) | 21.6 ± 7.3 | 68.3 ± 10.3 |
| Methionine (250 mg/kg) | 42.7 ± 7.2 | 156.8 ± 23.8 |

Table 8

Therapeutic effect on fatty liver - Histopathological examination -

| Group | Degree of fatty liver |
|---|---|
| Control | − − − − − |
| Positive control | + ++ + + + ++ |
| Compound 4 (50 mg/kg) | ± ± + ± ± ± + |
| ibid. (250 mg/kg) | ± ± ± − − − ± |
| Compound 1 (50 mg/kg) | ± + ± ± ± ± + |
| ibid. (250 mg/kg) | ± ± − − ± ± ± |
| Compound 2 (50 mg/kg) | ± ± + ± ± + ± |
| ibid. (250 mg/kg) | − − ± ± ± ± − |
| Methionine | ± ± ++ ++ ++ + + |

As shown in Table 7, the group "Positive control" to which carbon tetrachloride was administered but thereafter the compund of this invention was not administered manifested a high degree of fatty liver and showed no sign of improvement.

On the other hand, in the therapeutic groups to which the compound of this invention was given at the dose of 50 or 250 mg/kg the degree of fatty liver was significantly improved. In other words, the compound of this invention exhibited a therapeutic effect.

On the contrary, methionine hardly exhibited a therapeutic effect against fatty liver induced by carbon tetrachloride.

Table 8 illustrates the results of histopathological examination. The size and number of lipid droplet decreased in the groups therapied with the compounds of this invention, demonstrating an alleviation of fatty liver.

Accordingly, the compound of this invention is useful as pharmaceutical for fatty liver in humans and animals.

EXAMPLE 15

Cholagogic Action

Formation and excretion of biliary salt in the bile outflow are the important metabolic functions of the liver. If the bile flow is damaged by some cause, cholestasis and several types of liver diseases accompanying jaundice will be induced.

Drugs as choleresis are used for patients to improve bile flow. In the present example, the effect of the compound of the invention on the quantities of bile and biliary salt is investigated. Methods:

The male rats (4 week-aged, SD-JCL strain) were anesthetized with sodium pentobarbital (37.5 mg/kg, intraperitoneal injection). The abdominal cavity was opened through a midline incision. The common bile duct was catheterized with polyethylene tube o.d. 0.8 mm. The catheter was brought to the outside through the abdominal incision would prior to closing. Bile was collected from the catheter continuously with time intervals of one hour. The quantity of bile produced in one hour was determined by weighing and that of biliary salt was determined by enzymatic method (Ikagaku Jikkenho Koza 1B, Biological Constituents II, edited by Tamio YAMAKAWA). The amount of biliary salt was represented in the term of cholic acid equivalent.

In the representation of the results, the quantities of bile and biliary salt produced in one hour prior to the administration of drug were taken as 100. The compound of this invention was orally administered at the dose of 200 mg/kg. As reference, anethol trithion was used.

creted biliary salts for 5 hours after administration of Compound 1, Compound 2 and Compound 4 was 1.40, 1.43 and 1.37 times, respectively, greater than that in control. In the case of anethol trithion, however, no particular increase was observed in the excretion of biliary salt. In other words, the compounds of this invention were particularly effective in promoting the excretion of biliary salt.

The compounds of this invention are to be classified as drug for increasing the excretion of biliary salts, namely cholanertica, and their effectiveness to the disease of human and animal liver or bile duct can readily be expected from the hitherto reported findings concerning the behavior of anethol trithion. As above, the compounds of this invention can stimulate the metabolic function of the liver and therefore are useful as pharmaceutical for controlling liver damages caused by cholestegnosis.

EXAMPLE 16

Effect on Concentration of Ethyl alcohol in the Blood

The test compounds are dissolved or suspended in olive oil and administered orally at the dose of 250 mg/kg to the mice. After 6 hours, 1,000 mg/kg of ethyl alcohol was given orally. Blood was taken in a capillary Table 9
Results: Effect on bile flow

| | Experiment 1 | | Experiment 2 | | Experiment 3 | | Experiment 4 | |
|---|---|---|---|---|---|---|---|---|
| Time | Control | Compound 1 (200 mg/kg) | Control | Compound 2 (200 mg/kg) | Control | Compound 4 (200 mg/kg) | Control | Anethol trithion (200 mg/kg) |
| Before treatment 1 hour | 100 | 100 | 100 | 100 | 100 | 100 | 100 | 100 |
| After treatment | | | | | | | | |
| 1 hour | 100 ± 2.4 | 110 ± 1.8 | 100 ± 2.4 | 112 ± 2.4 | 100 ± 2.4 | 108 ± 2.1 | 104 ± 3.5 | 114 ± 15 |
| 2 hours | 104 ± 6.5 | 115 ± 6.8 | 104 ± 6.5 | 117 ± 6.8 | 104 ± 6.5 | 120 ± 7.7 | 101 ± 4.9 | 114 ± 15 |
| 3 " | 92 ± 6.4 | 105 ± 6.2 | 92 ± 6.4 | 101 ± 7.0 | 92 ± 6.4 | 107 ± 6.8 | 93 ± 6.9 | 102 ± 11 |
| 4 " | 88 ± 9.7 | 98 ± 8.2 | 88 ± 9.7 | 97 ± 8.3 | 88 ± 9.7 | 98 ± 7.2 | 84 ± 6.7 | 95 ± 7.7 |
| 5 " | 85 ± 9.3 | 80 ± 6.8 | 85 ± 9.3 | 80 ± 7.3 | 85 ± 9.3 | 88 ± 5.3 | 76 ± 6.6 | 86 ± 6.6 |

Table 10
Effect on the excretion of biliary salt

| | Experiment 1 | | Experiment 2 | | Experiment 3 | | Experiment 4 | |
|---|---|---|---|---|---|---|---|---|
| Time | Control | Compound 1 (200 mg/kg) | Control | Compound 2 (200 mg/kg) | Control | Compound 4 (200 mg/kg) | Control | Anethol trithion (200 mg/kg) |
| Before treatment 1 hour | 100 | 100 | 100 | 100 | 100 | 100 | 100 | 100 |
| After treatment | | | | | | | | |
| 1 hour | 89 ± 6.6 | 103 ± 6.8 | 89 ± 6.6 | 102 ± 7.3 | 89 ± 6.6 | 100 ± 7.2 | 94 ± 6.2 | 108 ± 12 |
| 2 hours | 92 ± 11 | 102 ± 6.6 | 92 ± 11 | 100 ± 5.8 | 92 ± 11 | 106 ± 7.8 | 89 ± 9.5 | 89 ± 11 |
| 3 " | 66 ± 8.8 | 100 ± 5.8 | 66 ± 8.8 | 106 ± 7.9 | 66 ± 8.8 | 98 ± 4.3 | 71 ± 11 | 66 ± 3.8 |
| 4 " | 54 ± 15 | 95 ± 7.7 | 54 ± 15 | 97 ± 7.2 | 54 ± 15 | 90 ± 7.7 | 56 ± 9.7 | 47 ± 3.0 |
| 5 " | 46 ± 16 | 86 ± 5.2 | 46 ± 1.6 | 90 ± 5.3 | 46 ± 16 | 82 ± 6.8 | 52 ± 10 | 3.3 ± 4.0 |

As shown in Table 9, bile flow was elevated by the administration of the compound of this invention. Quantity of total excreted bile for 5 hours after administration of Compound 1, Compound 2 and Compound 4 was 1.10, 1.13 and 1.11 times greater than that in control. On the other hand, the quantity of total excreted bile after administration of anethol trithion was 1.10 times greater than that in control.

As shown in Table 10, the amount of excreted biliary salt was remarkably increased by the administration of the compound of this invention. Amount of total exfrom caudal vein at the time indicated in the results. The plasma was obtained by centrifugation. The concentration of ethyl alcohol in the plasma was measured by FID type gas liquid chromatography. Five mice were used for each group.

Table II

| Time (min) | Result: Concentration of Ethyl alcohol in Plasma (ppm) | | | |
|---|---|---|---|---|
| | Control | Compd. Pre-treated | | |
| | | Compd. 1 | Compd. 2 | Compd. 4 |
| 0 | 27±17 | 12±3 | 10±7 | 9±4 |
| 5 | 875±203 | 732±102 | 711±95 | 730±92 |
| 15 | 810±191 | 710±88 | 558±104 | 536±113 |
| 30 | 690±214 | 455±112 | 426±96 | 373±105 |
| 60 | 167±76 | 12±7 | 13±6 | 7±2 |
| 120 | 5±1 | Not detected | Not detected | Not detected |

The concentration of ethyl alcohol in the plasma of the present compound-treated mice was lower than that of normal mice. This tendency was particularly marked at the stages of 30, 60 and 120 minutes after administration of ethyl alcohol, and thus it is understood that the amount of ethyl alcohol in the treated mice decreased quickly. Further, the present compound-treated mice were obviously quicker in recovery of intoxicated state, when observed visually. This indicates that by administration of the present compounds, the mice were stimulated in alcohol metabolic function of liver.

EXAMPLE 17

Effect on glucose metabolism:
Methods:

The test compounds dissolved in olive oil and administered orally at the dose of 250 mg/kg to the mice. After 6 hours, 4.0 g/kg of glucose was orally administered. The same amount of glucose was given to the control animals. 0.02 ml of blood was taken from caudal vein of the mice at 30, 60, 90 and 120 min. after glucose administration. Blood sugar was measured by the procedure of Somogyi-Nelson. Number of animals used was 5 to 6 mice for each treatment.

Table 12

| (min.) | Results: Blood Sugar (mg/dl) | | |
|---|---|---|---|
| | Time | Test Compound Pre-treatment | |
| | Control | Compd. 1 | Compd. 2 |
| 0 | 145±11.8 | 138±18.2 | 136±12.3 |
| 30 | 311±21.9 | 260±20.4 | 247±20.2 |
| 60 | 290±14.6 | 228±15.2 | 212±13.1 |
| 90 | 263±13.1 | 188±11.3 | 177±15.5 |
| 120 | 251±13.5 | 132±10.4 | 130±10.8 |

The blood sugar values of the each group showed peaks after 30 minutes, and no substantial difference was seen in the peak values. Thereafter, however, obvious difference was observed in the recovery of blood sugar value, and the present compound-treated groups were quicker in recovery. This indicates that by administration of the present compounds, the mice were stimulated in glucose metabolic function of liver.

What is claimed is:

1. A pharmaceutical composition for preventing liver necrosis, for preventing and curing hepatitis or fatty liver, and for formation and excretion of bile flow or biliary salt, which contains an effective amount sufficient for said purpose of a compound having the general formula, $$\begin{array}{c} R^1OC \\ \parallel \\ O \end{array} \diagdown C=C \diagup \begin{array}{c} S-CH-OR^3 \\ | \\ S-CH_2 \end{array} \\ R^2OC \diagup \\ \parallel \\ O$$

wherein $R^1$ and $R^2$, which may be the same or different, represent individually a $C_1$-$C_4$ alkyl group, and $R^3$ represents a hydrogen atom, an acetyl group or a propionyl group; and a pharmaceutically acceptable diluent.

2. A pharmaceutical composition of claim 1 which contains the said compound in an amount of at least 0.01% by weight.

3. The composition of claim 1, wherein the said compound is diethyl 4-hydroxy-1,3-dithiolan-2-ylidene malonate.

4. The composition of claim 1, wherein the said compound is diisopropyl 4-hydroxy-1,3-dithiolan-2-ylidene malonate.

5. The composition of claim 1, wherein the said compound is ethyl isopropyl 4-hydroxy-1,3-dithiolan-2-ylidene malonate.

6. The composition of claim 1, wherein the said compound is diisopropyl 4-acetoxy-1,3-dithiolan2-ylidene malonate.

7. The composition of claim 1, wherein the compound is formulated into an administration unit form.

8. The composition of claim 7, wherein the administration unit form is any one of powder, granule, tablet, pill, sugar-coated tablet, capsule, ampoule, suppository, suspension, liquid, emulsion or injection.

9. The composition of claim 7, wherein the said compound is diethyl 4-hydroxy-1,3-dithiolan-2-ylidene malonate.

10. The composition of claim 7, wherein the said compound is ethyl isopropyl 4-hydroxy-1,3-dithiolan-2-ylidene malenate.

11. The composition of claim 7, wherein the said compound is diisopropyl 4-hydroxy-1,3-dithiolan-2-ylidene malonate.

12. The composition of claim 7, wherein the said compound is diisopropyl 4-acetoxy-1,3-dithiolan-2-ylidene malonate.

13. A process for preventing liver necrosis, for preventing and curing hepatitis or fatty liver, and for formation and excretion of bile flow or biliary salt of animals including humans which comprises administering orally or parenterally to the animal an effective amount for said purpose of a compound having the general formula, $$\begin{array}{c} R^1OC \\ \parallel \\ O \end{array} \diagdown C=C \diagup \begin{array}{c} S-CH-OR^3 \\ | \\ S-CH_2 \end{array} \\ R^2OC \diagup \\ \parallel \\ O$$

wherein $R^1$ and $R^2$, which may be the same or different, represent individually a $C_1$-$C_4$ alkyl group, and $R^3$ represents a hydrogen atom, an acetyl group or a propionyl group.

14. The process of claim 13, wherein the administration is carried out parenterally.

15. The process of claim 14, wherein the dose is in the range from 0.01 to 250 mg per kg body weight per day.

16. The process of claim 13, wherein the administration is carried out orally.

17. The process of claim 16, wherein the dose is in the range from 0.01 to 500 mg per kg body weight per day.

18. The process of claim 13, wherein the compound is diethyl 4-hydroxy-1,3-diothiolan-2-ylidene malonate.

19. The process of claim 13, wherein the compound is ethyl isopropyl 4-hydroxy-1,3-dithiolan-2-ylidene malonate.

20. The process of claim 13, wherein the compound is diisopropyl 4-hydroxy-1,3-dithiolan-2-ylidene malonate.

21. The process of claim 13, wherein the compound is diisopropyl 4-acetoxy-1,3-dithiolan-2-ylidene malonate.

22. The process of claim 13, wherein said necrosis, fatty liver or hepatitis is induced by chemical poisoning.

23. The process of claim 22, wherein the chemical causing said poisoning is carbon tetrachloride, chloroform, bromobenzene, dimethyl-nitrosoamine, thioacetamide, allyl alcohol, D-Galactosamine, ethionine, a cadmium salt or a selenium salt.

24. The process of claim 13, wherein said liver necrosis, fatty liver or hepatitis has a histopathological symptom similar to that induced by chemical poisoning.

25. The process for lowering the concentration of alcohol in the blood of animals including humans comprising administering orally or parenterally to the animal an effective amount sufficient for said purpose of a compound having the general formula, $$\begin{array}{c} R^1OC \\ \parallel \\ O \end{array} C=C \begin{array}{c} S-CH-OR^3 \\ | \\ S-CH_2 \end{array}$$
$$R^2OC$$
$$\parallel$$
$$O$$

wherein $R^1$ and $R^2$, which may be the same or different, represent individually a $C_1$–$C_4$ alkyl group, and $R^3$ represents a hydrogen atom, an acetyl group or a propionyl group.

26. The process of claim 25, wherein the compound is diethyl 4-hydroxy-1,3-dithiolan-2-ylidene malonate.

27. The process of claim 25, wherein the compound is ethyl isopropyl 4-hydroxy-1,3-dithiolan-2-ylidene malonate.

28. The process of claim 25, wherein the compound is diisopropyl 4-hydroxy-1,3-dithiolan-2-ylidene malonate.

29. The process of claim 25, wherein the compound is diisopropyl 4-acetoxy-1,3-dithiolan-2-ylidene malonate.

30. A process for treating diabetes in animals including humans comprising administering orally or parenterally an effective blood-sugar depressant amount to said animal for stimulating the sugar metabolic function of the liver to lower the abnormally elevated concentration of sugar in the blood of a compound having the general formula, $$\begin{array}{c} R^1OC \\ \parallel \\ O \end{array} C=C \begin{array}{c} S-CH-OR^3 \\ | \\ S-CH_2 \end{array}$$
$$R^2OC$$
$$\parallel$$
$$O$$

wherein $R^1$ and $R^2$, which may be the same or different, represent individually a $C_1$–$C_4$ alkyl group, and $R^3$ represents a hydrogen atom, an acetyl group or a propionyl group.

31. The process of claim 30, wherein the compound is diethyl 4-hydroxy-1,3-dithiolan-2-ylidene malonate.

32. The process of claim 30, wherein the compound is ethyl isopropyl 4-hydroxy-1,3-dithiolan-2-ylidene malonate.

33. The process of claim 30, wherein the compound is diiospropyl 4-hydroxy-1,3-dithiolan-2-ylidene malonate.

34. The process of claim 30, wherein the compound is diisopropyl 4-acetoxy-1,3-dithiolan-2-ylidene malonate.

* * * * *